United States Patent [19]

Beard, Jr. et al.

[11] Patent Number: 4,928,294
[45] Date of Patent: May 22, 1990

[54] METHOD AND APPARATUS FOR LINE-MODIFIED ASYMMETRIC CRYSTAL TOPOGRAPHY

[75] Inventors: Warren T. Beard, Jr., Upper Marlboro; Ronald W. Armstrong, Edgewater, both of Md.

[73] Assignee: U.S. Government as represented by the Director, National Security Agency, Fort George G. Meade, Md.

[21] Appl. No.: 330,348

[22] Filed: Mar. 24, 1989

[51] Int. Cl.$^5$ .............................................. G01N 23/20
[52] U.S. Cl. .......................................... 378/74; 378/84
[58] Field of Search ............................. 378/74, 73, 84

[56] References Cited

U.S. PATENT DOCUMENTS 3,982,127  9/1976  Hartmann et al. .................... 378/74

Primary Examiner—Craig E. Church
Attorney, Agent, or Firm—Thomas O. Maser; John R. Utermohle

[57] ABSTRACT

An improved asymmetric crystal topography x-ray imaging system employing a fine focus horizontal line source of x-rays and a crystal monochromator used in a compression mode. Relatively large horizontal and vertical dimensions of the monochromating crystal allow imaging of larger areas of imperfect crystals than previously possible, without adversely affecting image resolution. The high resolution two-dimensional images are a direct consequence of our method of controlling the probe beam divergences. An appreciably enhanced and useful intensity of monochromatic x-rays is obtained over that available with prior asymmetric crystal topography systems.

13 Claims, 5 Drawing Sheets

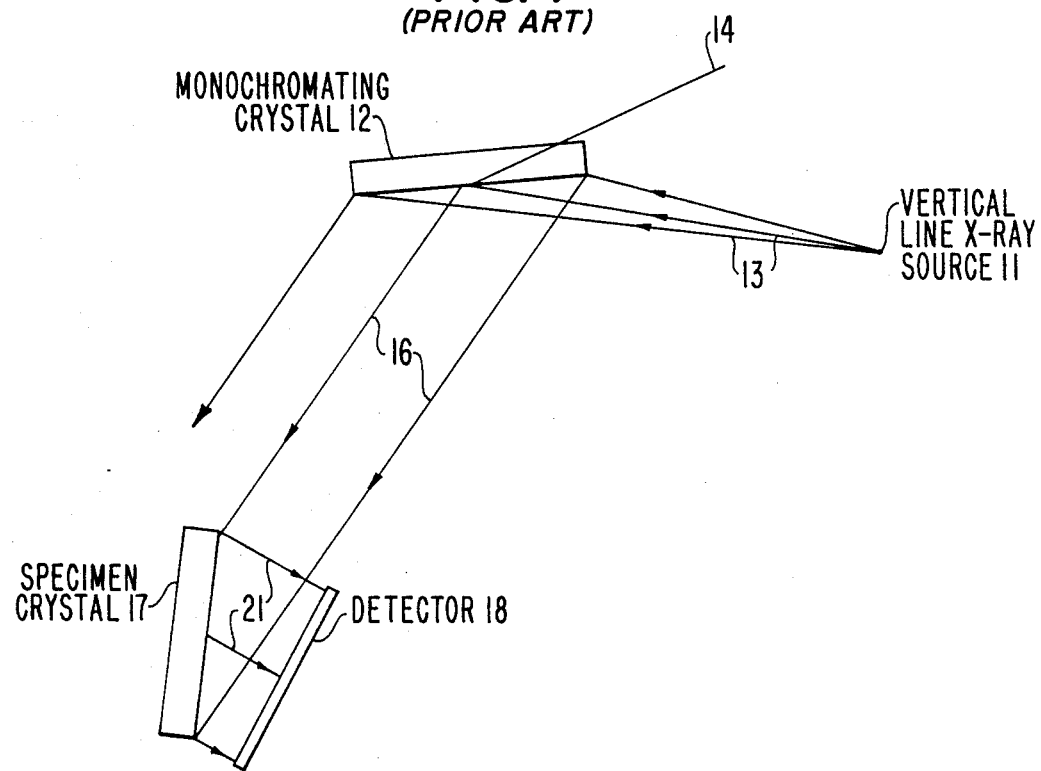
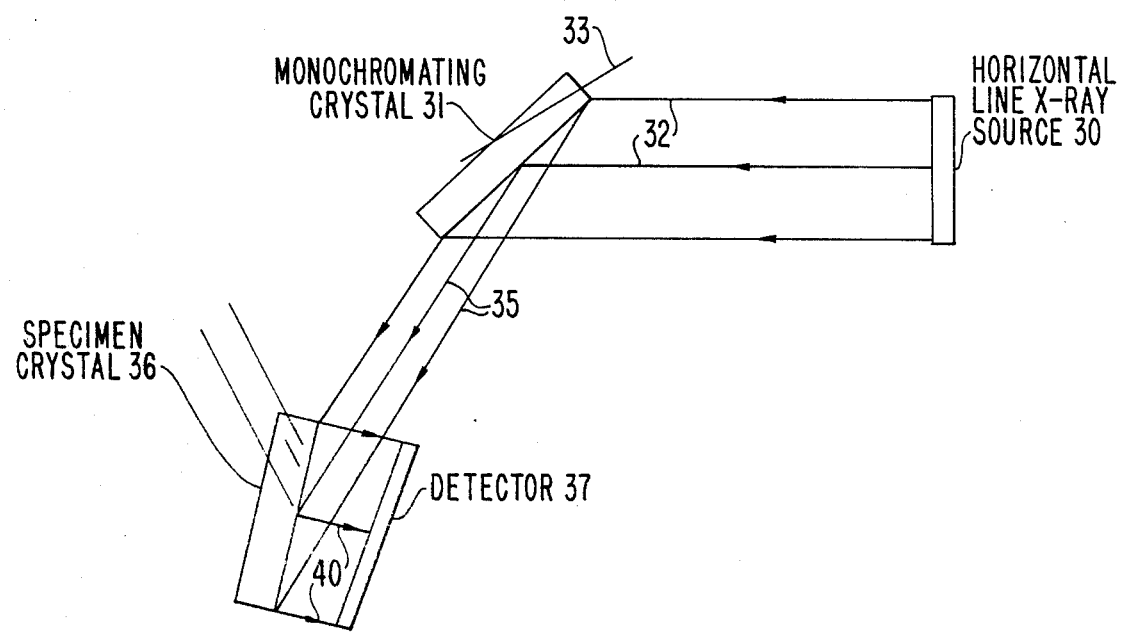

FIG. 3
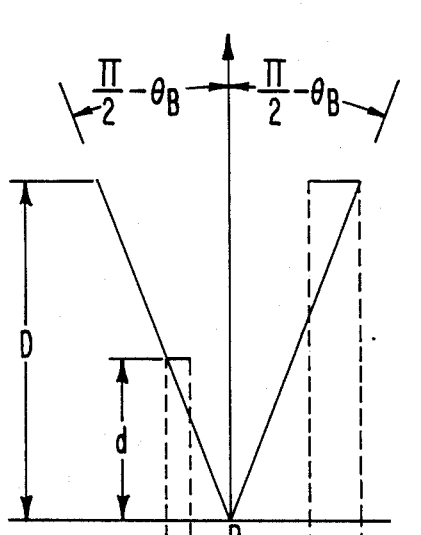
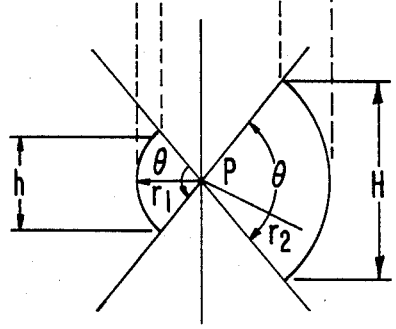
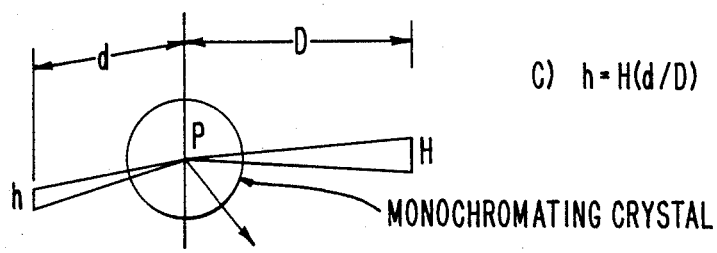
A) SIDE VIEW
  D = SOURCE TO CRYSTAL DISTANCE
  d = CRYSTAL TO FILM DISTANCE
B) TOP VIEW
  H = HORIZONTAL LINE SOURCE HEIGHT
  h = IMAGE HEIGHT OF CRYSTAL POINT P AT THE FILM
$$\frac{r_1 \theta}{r_2 \theta} \propto \frac{h}{H} = \frac{d}{D}$$
C) $h = H(d/D)$

| $h = H\{d_2/[d_1+D+d_2(1-H/M)]\}$ | | |
|---|---|---|
| H = 0.04 mm | | M = 25.4 mm |
| D (cm) | h = 0.2 μm<br>$d_1$ (cm) WITH $d_2$ = 3.0 mm | h = 0.3 μm<br>$d_1$ (cm) WITH $d_2$ = 3.0 mm |
| 50.0 | 9.7 | — |
| 30.0 | 29.7 | 9.7 |
| 10.0 | 49.7 | 20.7 |

METHOD AND APPARATUS FOR LINE-MODIFIED ASYMMETRIC CRYSTAL TOPOGRAPHY

BACKGROUND OF THE INVENTION

1. Field of the invention.

Our invention relates to the field of non-destructive testing, and more particularly, to high resolution imaging of internal strains in crystal structures.

2. Description of the related art.

Semiconductor fabrication processes are requiring larger and more perfect crystals. Currently, routine integrated circuit (IC) testing is dominated by measurement of the optical and electrical material/device properties through final device performance and parametric testing. The occurrence of internal flaws, such as those which may relate even to the internal microstructure of the substrate crystal, may result in an entire production run being worthless. Obviously, flaws detected only after completion of the production run are found too late to allow for corrective action.

While methods for the characterization of internal strains or flaws within crystal microstructures are known, these methods are not yet considered sufficiently insightful or necessary to be a routine part of the IC fabrication process. Known procedures for analyzing the degree of perfection of a crystal structure include the use of double-crystal rocking curves (see X. Chu and B. K. Tanner, "Double Crystal X-Ray Rocking Curves of Multiple Layer Structures," *Semicond. Sci. Technol.* 2: 765, 1987), x-ray topography (see G. A. Rozogonyi and D. Miller, "X-Ray Characterization of Stresses and Defects in Thin Films and Substrates," *Methods and Phenomena 2-Characterization of Epitaxial Semiconductor Films*. H. Kressel, ed., Elsevier Scientific Publishing Co., 1976, p. 185), or a combination of these techniques.

The x-ray diffraction topography method is capable, in principle, of visually revealing lattice strains and misorientations over large crystal areas. Recently, it has been demonstrated that such topography information can be used to correlate lattice strain and device performance in silicon integrated circuits (see S. B. Qadri, D. Ma, and M. Peckerar, "Double-Crystal X-ray Topographic Determination of Local Strain in Metal-Oxide Semiconductor Device Structures," *Appl. Phys. Lett.* 51: 1827 [1987]). Many different x-ray topography geometries have been used to date, and each system has its own advantages. The conventional Asymmetric Crystal Topography (ACT) system gives excellent measurements of small angular misorientations potentially occurring in relatively large, nearly perfect single crystals (see W. J. Boettinger, H. E. Burdette, M. Kuriyama, R. E. Green, Jr., "Asymmetric Crystal Topographic Camera," *Rev. Sci. Instrum.*, v. 47, No. 8, August 1976, p. 906). Another topography technique is known to reveal local dislocation images with excellent spatial resolution (A. R. Lang, *Diffraction and Imaging Techniques*, v. 2, North-Holland, Amsterdam, 1978, p. 678). Superior resolution of individual dislocations and their accumulated strain fields has been obtained using the Berg-Barrett topography technique in a configuration with a limiting small specimen to recording media distance, as specified by Newkirk (J. B. Newkirk, "The Observation of Dislocations and other Imperfections by X-ray Extinction Contrast," *Trans. Metallurgical Soc. AIME*, v. 215, June 1959, p. 431).

A detailed analysis of semiconductor material and associated integrated circuits is imperative for ensuring quality products. To date, there is no effective nondestructive technique which has both high vertical and high horizontal resolution and which can be used after each step in the production process and still allow the wafer to be reinserted for further processing. A desirable process must provide fine angular resolution in diffraction images of varying crystal orientations spread over large areas. It must have optimum spatial resolution over a large area, with minimal time required for equipment set-up and exposure of the recording media. Finally, high resolution must be obtainable with reasonable working distances between an inspection-beam-forming x-ray monochromating crystal, the crystal specimen to be examined, and the image recording media capturing, non-destructively, a picture of the internal crystal strains and misorientations.

SUMMARY

We have invented an improved method and apparatus for nondestructively analyzing the internal structure of crystals. The improved method and apparatus provide the advantages identified above.

It is an object of our invention to provide an apparatus for nondestructive analysis of IC crystal structure.

A further object is to provide, by means of geometric beam compression, an inspecting x-ray beam of high geometric resolution with minimal loss of beam energy density.

Another object is to expand the area of crystal which will be imaged beyond that for monochromated point source of x-rays with minimum reduction of spatial resolution.

Finally, it is an object to provide a high resolution large two-dimensional x-ray image of the crystal specimen being examined.

The important elements of our invention include: a horizontal line x-ray beam source; means having a surface illuminated by said x-ray beam and oriented in a beam compression mode with respect to said x-ray beam for producing a first diffracted beam; a specimen to be imaged, said specimen illuminated by, and oriented with respect to, said first diffracted beam such that a second diffracted beam is obtained from said specimen, and a detector for recording said second diffracted beam.

A method for high resolution x-ray imaging of a crystal according to our invention would include: projecting a horizontal line x-ray beam onto a monochromating crystal; diffracting said beam at an angle relative to the surface of the crystal such that the quantity of energy diffracted at the surface of the crystal is maximized while the horizontal and vertical divergence of the diffracted beam are minimized; projecting the diffracted beam onto a specimen crystal; and diffracting the diffracted beam at an angle relative to the surface of the specimen crystal such that the angle of the diffracted beam relative to the normal of the specimen crystal is minimized.

BRIEF DESCRIPTION OF THE DRAWINGS

Our invention may be best understood when the following specification is read together with the drawings, in which:

FIG. 1 illustrates a prior art Asymmetrical Crystal Topography imaging system;

FIG. 2 illustrates a Line-Modified Asymmetrical Crystal Topography imaging system embodying the essential elements of our invention;

FIG. 3 is a graphic representation of the relationship between the source beam height and the image height of our invention;

BRIEF DESCRIPTION OF THE PREFERRED EMBODIMENT

Figure 4A:
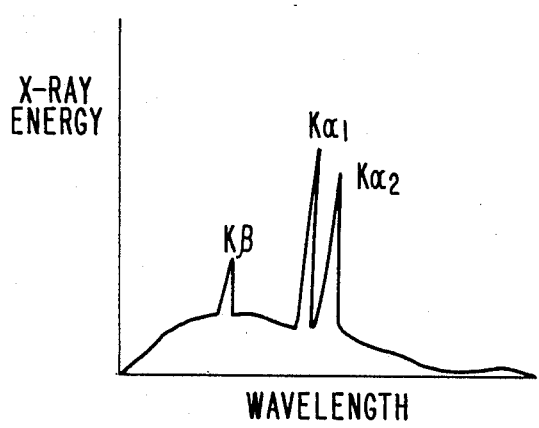
FIGS. 4a and 4b are illustrative plots of x-ray energy vs wavelength of the polychromatic vertical line x-ray source and the monochromatic specimen illuminating beam of the prior art.

FIG. 1 illustrates a top view of an ACT imaging system representative of the prior art. It includes a vertical line x-ray source 11 which illuminates a monochromator crystal 12 with a beam 13. A first diffracted x-ray beam 16 illuminates a specimen crystal 17. A detector 18 is positioned to receive a second diffracted beam 21. Crystal 12 operates in a beam expansion mode, determined by the orientation of the crystal structure with respect to the incident beam. Plane 14 represents one of the family of parallel diffraction planes defined by the crystal structure in this particular embodiment.

FIG. 2 illustrates a top view of a Line Modified Asymmetric Crystal Topography (LMACT) imaging system containing the essential features of our invention. It includes a horizontal line x-ray source 30 which illuminates a monochromator crystal 31 with a beam 32. The monochromator crystal 31 may be silicon, gallium arsenide or any reasonable quality crystal structure providing diffracting planes and producing a specular uniform diffracted beam. The surface of monochromator crystal 31 must be cut relative to the family of diffracting plane such that there is an asymmetry between the incident angle and diffracted angle of beam 32. The resulting diffracted beam 35 will then contain the maximum amount of energy density from the incident beam 32. In the vertical dimension, the horizontal line source is a point source. From that point eminating rays are isotropic and are incident on the monochromating crystal in a very small solid angle. This results in very low vertical divergence in beam 35. The horizontal divergence is controlled by the full-width-half-maximum of the Bragg diffraction from monochromating crystal 31.

Plane 33 represents one of the family of parallel diffraction planes defined by the crystal structure in this particular embodiment. A diffracted x-ray beam 35 illuminates a specimen crystal 36. Specimen crystal 36 may be single crystal sodium chloride, silicon, gallium arsenide, or any crystal structure providing diffracting planes which produce a diffracted beam projected close to the specimen surface normal. A detector 37 is positioned to receive the diffracted beam 40. Detector 37 might be photographic film, a charge-coupled device, or other appropriate device for detecting and recording the diffracted x-ray energy. It is important, however, that the resolution capability of the detector be fine enough to retain the improved spatial resolution provided by the beam diffracted from the specimen crystal.

The characteristics of crystal 31 are selected by criteria based on the specimen to be analyzed. The orientation of any crystal surface normal to the internal diffracting plane normal determines the asymmetry of the incident and reflected beam angles. In the monochromating crystal, this fixes the compression or expansion in the x-ray probe beam. Beginning with the specimen crystal, one would select both the set of diffracting planes to be used and the horizontal distance to be imaged. The known diffraction planes and surface orientations of the specimen crystal will allow calculation of the incident angle of the inspecting monochromatic x-ray beam onto the specimen crystal. With the incident angle and the horizontal distance to be imaged both selected, one can calculate the required width of the incident beam onto the specimen. This is the width of the beam chosen to be diffracted from the monochromating crystal. Knowing this projected width and the actual monochromating crystal width allows determination of the required compression ratio. It is necessary to select a set of diffracting planes used in the monochromating crystal. Using that set of planes and the compression ratio, one can calculate the cutting angles necessary to provide the surface orientation of the monochromating crystal which result in the proper probe beam width.

By comparing the prior art apparatus of FIG. 1 with the apparatus of our invention illustrated in FIG. 2, two distinctions are readily apparent. First, the vertical line x-ray source 11 of the prior art has been replaced with the horizontal line x-ray source 30 of our invention. Second, the monochromator crystal 12 orientation, represented by plane 14, has been altered so that the beam expansion previously provided in FIG. 1 is now replaced by a beam compression in our invention. The significant improvements in spatial resolution achieved by our invention are the direct result of this new design and its consequent modifications of the x-ray probe beam.

The use of a vertical line source 11 as practiced in the prior art provides a high resolution image in the horizontal orientation, but very limited vertical resolution is obtained for extremely small sample-detector distances (e.g., <1 mm). The obvious result is that it is necessary to take at least two images of the sample; one rotated 90° from the other, in order to have an accurate description of the sample. Our invention, on the other hand, provides only a trivially lower horizontal resolution while providing a vertical resolution 100 times higher than in the prior art. These combined results are achieved within a single image.

FIG. 3 shows the geometric interpretation of how the probe beam divergence is related to the image height of an ideal point on any crystal. The divergence angle ($\theta$) is the same for incident and diffracted beams, and results in an image which can be much larger than the actual area where diffraction occurred. This equation is extended to the specific case of our invention in FIG. 7a.

Figure 4B:
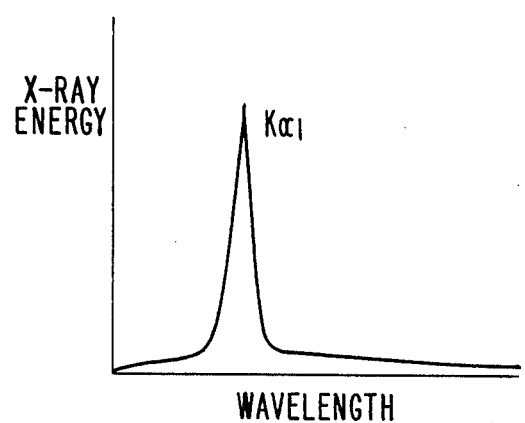
Figure 5A:
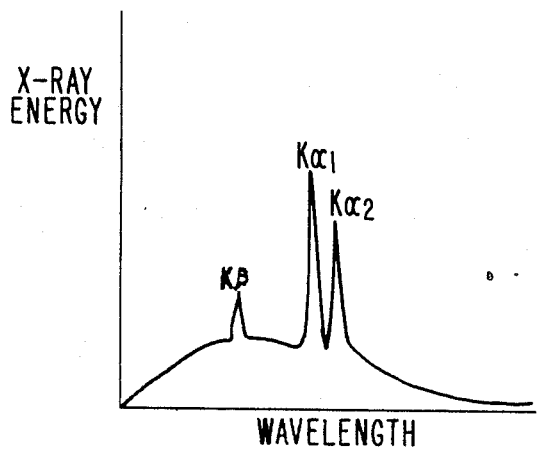
FIGS. 5a and 5b are illustrative plots of x-ray energy vs wavelength of the polychromatic horizontal line x-ray source and the dichromatic specimen illuminating beam of our invention.
Figure 5B:
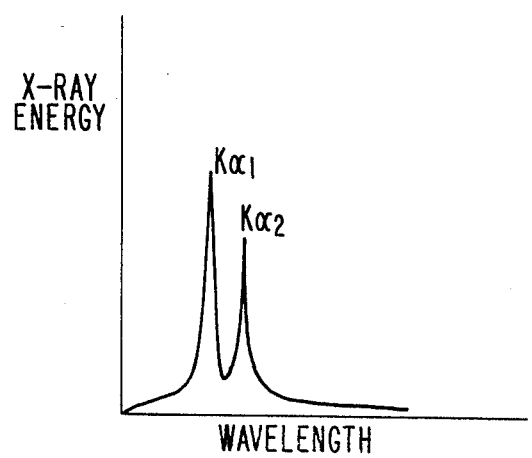

FIGS. 4 and 5 allow a spectral comparison of the effects of beam compression as practiced in our invention with the effects of beam expansion as practiced in the prior art. Obviously, the x-ray energy spectra emitted from the horizontal source is identical to that emitted from the vertical source, as is illustrated in FIGS. 4a and 5a. The compressed beam illustrated in FIG. 5b, however, includes both the K$\alpha_1$ and the K$\alpha_2$ wavelengths because both monochromatic wavelengths are able to be diffracted simultaneously at slightly different angles in the horizontal plane. With the expansion beam of the prior art, however, the beam diffracted from the monochromating crystal towards the sample crystal includes only one or the other of the K$\alpha$ wavelengths. This is because one or the other of the K$\alpha$ beams is diffracted at an angle significantly different enough relative to the low horizontal divergence of the conventional ACT vertical line geometry to not be intercepted by the specimen crystal. However, horizontal image resolution in the Line-Modified Asymmetrical Crystal Topography system is still controlled by the perfect crystal angular reflecting width which is very small.

DESCRIPTION OF EXPERIMENTAL RESULTS

Figure 6:
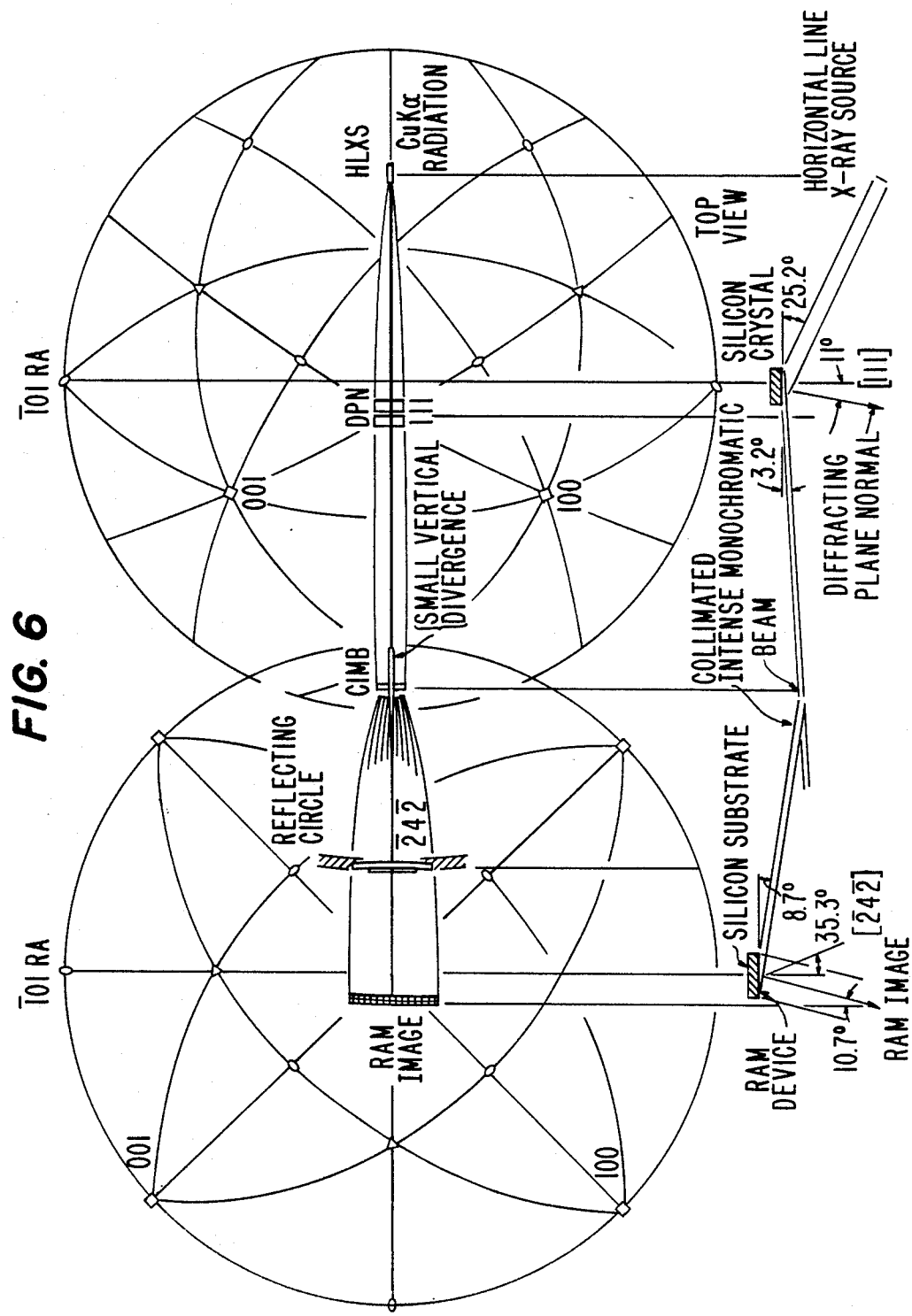
FIG. 6 is a coupled stereographic projection for a silicon monochromating crystal and a silicon random access memory specimen tested by the inventors to prove the utility of the invention, and FIG. 7a defines distances explained in the table of FIG. 7b.

FIG. 6 is a coupled stereographic projection for a silicon monochromating crystal and a silicon random access memory specimen tested by the inventors to prove the utility of the invention. Coupled stereographic projections of the monochromating crystal and specimen crystal are shown with the monochromating crystal on the right. A schematic view of the test apparatus is illustrated below the coupled stereographs. The coupled stereographs show along the equatorial plane that the vertical divergence at the specimen is controlled by the source height and the source-to-specimen total distance.

In the representation of FIG. 6, the horizontal line source is 0.04×8.0 mm$^2$. The silicon monochromating crystal is asymmetrically cut 11° off the (111) toward the [010]. Using the (111) Bragg reflection ($\theta_B$=14.22°, CuK$\alpha_1$) rotated about the [$\bar{1}$01] axis, the x-ray incidence angle relative to the crystal surface is 25.22° and the reflection angle relative to the surface is 3.22°. A compression ratio of (sin 3.22° /sin 25.22°) =0.132 produces a reflected beam from the monochromator which is collimated and intensified, and which contains both K$\alpha_1$ and K$\alpha_2$ wavelength components. In FIG. 6, this is the collimated intense monochromatic beam (CIMB). The beam height is limited by the monochromating crystal height which is approximately 3 cm.

The (010) face of a silicon-based RAM device was set for Bragg reflection from the inclined ($\bar{2}4\bar{2}$) plane ($\theta_B$=44.0°, CuK$\alpha_1$) when the wafer was rotated 8.7° about the [$\bar{1}$01] axis. The zero reference for the rotation is taken as the position where the incident x-ray beam is parallel to the crystal surface. With the [$\bar{2}4\bar{2}$] diffracting plane normal positioned within the reflecting circle at an angle of ($\pi/2$0-$\theta_B$ from the CIMB, the RAM device image emerges from the specimen surface at 10.7° away from the device surface normal. The near orthogonal exit beam direction allows for capturing the image close to the device 15 surface. This is important to minimize the effect of the emergent intensity from each point on the crystal surface. The vertical divergence from a point on the crystal specimen looking towards the x-ray source is ($\Delta\beta$=0.04 mm/406.4 mm) 9.84×10$^{-5}$ radians (20.3 arcsec).

Figures 7A, 7B:
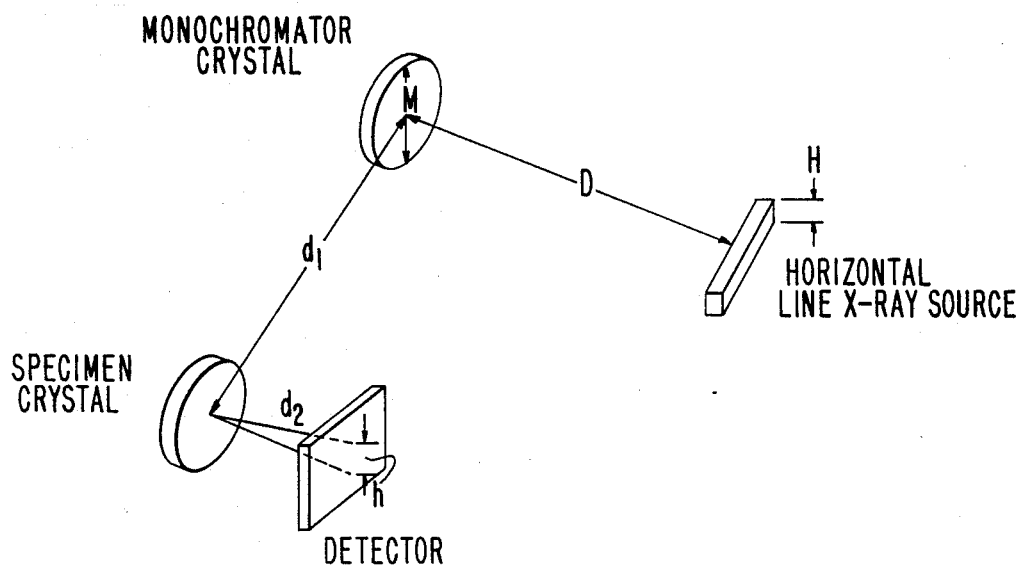

FIGS. 7a and 7b illustrate the relationship between the source beam height (H) and the image height (h). They show that control of the source height is critical in providing small vertical divergence and high horizontal resolution. They also show how this divergence can be controlled by the source-specimen and specimen-detector distances. The vertical resolution limit (h) of our technique is:

$$h = H\{d_2/[d_1 + D + d_2(1 - H/m)]\}$$

where H is the source height, D is the source-to monochromator distance, m is the monochromator crystal height, $d_1$ is the monochromator-to-specimen distance, and $d_2$ is the specimen-to detector distance. Representative numerical values for this equation have been presented in the table of FIG. 7b, and from these data one sees a vertical resolution of 0.3 $\mu$m is easily achieved with a sample-to-detector distance of 3.0 mm. This is in direct contrast to all other topography techniques which require sample-to-detector distances of less than 1 mm.

The equation for vertical resolution shows that $d_2$ should be minimized for highest resolution (smallest h). Our experimental indicate that at 3.0 mm=$d_2$, the K$\alpha_1$ and K$\alpha_2$ diffracted images are separated at the detector as a result of the different Bragg angles for the K$\alpha_1$ and K$\alpha_2$ diffractions from the specimen crystal. Any attempt to minimize $d_2$ must consider the overlap of the images produced by the K$\alpha_1$ and K$\alpha_2$ wavelengths in the incident x-ray beam. For values of $d_2$ approximately 1 mm, the image overlap will result in a change in horizontal resolution of a fraction of a micron.

While we have described a preferred embodiment of the invention based on our own experiments and demonstrated results, it will be readily apparent to one skilled in the art that several alternative embodiments will also achieve the same results without departing from the teachings we have provided. For example, while the preferred embodiment is illustrated with the monochromator crystal and the specimen crystal oriented with their surface normal in essentially the same directions (+n, +n), it is well known in the art that a similar result can be achieved by orienting the respective crystals with their surface normals in opposition (+n, −n). We intend that our invention be understood to include all well known orientations of the crystals and other elements to achieve the same results. The scope of our invention is defined in the claims which follow.

We claim:

1. An apparatus for high resolution x-ray imaging comprising:
   a horizontal line x-ray beam source;
   means having a surface illuminated by said x-ray beam and oriented in a beam compression mode with respect to said x-ray beam for producing a first diffracted beam;
   a specimen to be imaged, said specimen illuminated by, and oriented with respect to, said first diffracted beam such that a second diffracted beam is obtained from said specimen, and
   a detector for recording said second diffracted beam.

2. The apparatus of claim 1 wherein said diffracting means is a monochromating crystal.

3. The apparatus of claim 2 wherein said monochromating crystal has a diffracting plane asymmetrically oriented with respect to said illuminated surface.

4. The apparatus of claim 3 wherein said diffracting plane is fully illuminated by said x-ray beam.

5. The apparatus of claim 3 wherein said specimen is a crystal.

6. The apparatus of claim 5 wherein said monochromating crystal and specimen crystals are silicon crystals.

7. The apparatus of claim 5 wherein said monochromating crystal and specimen crystals are gallium arsenide crystals.

8. The apparatus of claim 5 wherein said monochromating crystal is a silicon crystal and said specimen crystal is a gallium arsenide crystal.

9. The apparatus of claim 1 or 5 wherein said detector is photographic film.

10. The apparatus of claim 1 or 5 wherein said detector is a charge-coupled device.

11. The apparatus of claim 1 wherein said first diffracted beam is a dichromatic beam.

12. The apparatus of claim 1 wherein said x-ray beam source is a polychromatic source.

13. A method for high resolution x-ray imaging of a crystal comprising:
   projecting an x-ray beam from a horizontal line source onto a monochromating crystal;
   diffracting said beam at an angle relative to the surface of the crystal such that the quantity of energy diffracted at the surface of the crystal is maximized while the horizontal and vertical divergence of the diffracted beam are minimized;
   projecting the diffracted beam onto a specimen crystal; and
   diffracting the diffracted beam at an angle relative to the surface of the specimen crystal such that the angle of the diffracted beam relative to the normal of the specimen crystal is minimized.

* * * * *